(12) United States Patent
Weir et al.

(10) Patent No.: US 6,921,419 B2
(45) Date of Patent: Jul. 26, 2005

(54) EXTERNALLY-POWERED HAND PROSTHESIS

(75) Inventors: Richard F. Weir, Evanston, IL (US); Edward C. Grahn, Arlington Heights, IL (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 30 days.

(21) Appl. No.: 10/717,481

(22) Filed: Nov. 21, 2003

(65) Prior Publication Data

US 2004/0117034 A1 Jun. 17, 2004

Related U.S. Application Data

(60) Provisional application No. 60/432,675, filed on Dec. 12, 2002.

(51) Int. Cl.[7] .................................................. A61F 2/54
(52) U.S. Cl. ........................................... 623/64; 901/38
(58) Field of Search ...................... 623/63, 64; 294/25, 294/28; 901/30, 31, 38, 39

(56) References Cited

U.S. PATENT DOCUMENTS

| | | | |
|---|---|---|---|
| 4,021,866 A | 5/1977 | Wasko | |
| 4,258,441 A | 3/1981 | Bell | |
| 4,291,421 A | 9/1981 | Massey | |
| 4,865,929 A | 9/1989 | Eck | |
| 4,990,162 A | 2/1991 | LeBlanc | |
| 5,116,386 A | 5/1992 | Scribner | |
| 5,222,986 A | 6/1993 | Wright | |
| 5,888,246 A | 3/1999 | Gow | |
| 6,423,099 B1 * | 7/2002 | Iversen et al. | ................. 623/64 |

* cited by examiner

*Primary Examiner*—Bruce E Snow
(74) *Attorney, Agent, or Firm*—Dykema Gossett PLLC

(57) ABSTRACT

An externally-powered prosthesis mechanism usable with persons with amputations at or proximal to the level of the metacarpophalangeal joint, as well as persons with high-level amputations. The prosthesis mechanism includes a grasping mechanism including a mechanically operable finger member and a mechanically operable thumb member kinematically linked to the finger member such that the grasping mechanism is disposed in respective opened and closed configurations when the finger member is respectively moved away from and toward the thumb member. The prosthesis mechanism further includes a drive system extending tangentially with respect to the grasping mechanism and including a motor operatively connected to drive at least one planetary gear stage, which is operatively connected to drive the grasping mechanism to the opened configuration when the motor is driven in a first direction and further drive the grasping mechanism to the closed configuration when the motor is driven in a second opposite direction.

19 Claims, 10 Drawing Sheets

EXTERNALLY-POWERED HAND PROSTHESIS

RELATED APPLICATIONS

This application claims benefit of priority of Provisional Application Ser. No. 60/432,675, filed Dec. 12, 2002.

BACKGROUND OF INVENTION a. Field of Invention

The invention relates generally to prosthesis devices, and, more particularly to an externally powered hand prosthesis mechanism for use with persons with amputations at or proximal to the level of the metacarpophalangeal joint, as well as persons with high-level amputations.

b. Description of Related Art

For people who have experienced the partial loss of a limb such as the hand, prosthetic solutions are generally considered only after reconstructive surgical procedures have failed. In cases where a thumb is amputated or otherwise lost, an opposition post, cosmetic or not, is usually prescribed. With an intact thumb however, even if the metacarpals have been somewhat shortened, an orthotic device can be fitted for providing a post for the uninjured thumb to oppose. Alternatively a static cosmetic prosthesis may be fitted instead of the orthotic device. For cases that require a specialized fitting however, such fittings usually take the form of a custom made work prosthesis and/or a cosmetic glove for social occasions.

In many cases involving the loss of a thumb, transmetacarpal amputations of the fingers are often associated with loss of the thumb at or proximal to the metacarpophalangeal joint. In such cases, an active functional hand prosthesis is generally recommended only for cases where all digits (thumb and all four fingers) have been lost at a level equal or proximal to the metacarpophalangeal joint.

The range of prosthetic devices presently available for people with partial hand amputations can be broadly divided into the following three general categories; cosmetic prostheses, passive functional prostheses, and active functional prostheses. Active functional prostheses may be further subdivided into body-powered and externally-powered devices.

Cosmetic prostheses for persons with partial hand amputations typically consist of a handlike cosmetic glove, generally with the missing fingers filled with a urethane foam with wire reinforcements running through them. For persons whose loss is not severe enough to merit a full glove, individual cosmetic digits (i.e. fingers/thumbs) may be worn. A lack of adequate retention is however sometimes an issue with such individual prostheses for which adhesives and adhesive tape are often used for retention. Traditionally, cosmetic gloves are made of polyvinyl-chloride (PVC), while silicone is the material of choice for "high-end" cosmetic coverings.

Passive functional prostheses, also commonly known as task specific prostheses, are prosthetic devices donned when needed and thereafter removed once the task for which they are designed has been completed. The majority of such devices are work prostheses that bare little or no resemblance to the natural hand. Examples of such devices include perhaps a simple post for providing opposition, or a device incorporating specialized features to aid in the performance of specific occupations.

Lastly, body-powered prosthetic devices are generally functional prostheses that use some of the body's motion for providing the excursion necessary to actuate opening and closing of the device. Such body-powered prostheses for people with partial-hand amputations fall, for the most part, into one of two groups, those devices that are powered by biscapular abduction and/or gleno-humeral flexion, and those devices that are powered by flexion or extension of the wrist.

For a person with bilateral partial-hand amputations, a shoulder-driven device is often the system of choice, the control mechanism for which consists of a figure-of-nine harness that fits about the shoulders and a cable that runs from the harness to an appropriate terminal device. The most common terminal devices take the form of a hook. The disadvantages of such devices include poor cosmesis and the requirement for a harness and control cable to be worn, even though these devices do preserve the residual motion of the wrist.

One such device, known as the "Handy Hook," uses a hook attached to the palmar surface of a partial hand prosthesis socket. Once attached through the use of a wrist attachment, the combination of the hook and wrist become one of the most functional prosthetic fittings, since wrist motion was preserved to assist the prehension process. One of the main disadvantages associated with this device however was that an individual had to wear a harness.

Another such system, known as the "Robin Aids Hand," attempted to provide both function and cosmesis for body-powered partial hand fittings, and consisted of mechanical fingers that had interchangeable components which were mounted on a very short frame. This device was a voluntary opening device that could be fitted on patients who had either their thumb intact, small and ring fingers remaining, or no digits remaining. The thumb was an independent two-position unit, which allowed a larger grasp for items such as a glass or bottle after passive pre-positioning. As with the aforementioned "Handy Hook," the "Robin Aids Hand" also required a harness and additionally a control cable. This device was also inefficient in operation and cosmetically displeasing. Whereas technological improvements have led to the development of more advanced body-powered prosthetic devices, such devices nevertheless restrict the work envelope of the amputee since tension in the control cable is required to actuate the terminal device. Since tension is not possible in all positions, the most common problem with such shoulder harness devices is that they cannot be stretched above the head, in which case the control cable becomes slack and sufficient tension cannot be developed to actuate the device. Another awkward position for such devices is in bending over to pick an object from the floor, in which case the control cable becomes too taut and cannot be slackened off to allow the terminal device to be driven.

For the second type of body-powered partial-hand prostheses, also referred to as wrist flexion and extension devices, such devices are functional cosmetic hands that operate in a manner similar to a tenodesis type hand orthosis (i.e. "tenodesis action" is a method by which prehension of the index finger, middle finger, and thumb is achieved through active wrist extension). These devices essentially operate by means of a linking mechanism which translates wrist extension into finger pinch and wrist flexion into finger opening. The user can thus determine where the fingers are and the forces involved through the wrist. This method is used extensively in Europe in the fitting of persons with partial hand amputation.

These aforementioned body-powered devices include drawbacks in that any remaining motion of the wrist that would normally be used to position a prehensor in space must be restricted to one degree-of-freedom (extension/flexion of the wrist) in order to drive the opening and closing of the terminal device. Additionally, while existing body-powered devices in general are aesthetically pleasing when static, their operation requires unnatural motions.

With regard to externally-powered prosthetic devices, such devices include for example externally-powered partial hand prosthesis for trans-carpal amputations. Such existing devices however are not suitable for amputations at the meta-carpophlangeal level, and do not preserve any residual motion of the wrist due to their size. An existing externally powered device for persons with partial hand amputations uses a single transverse motor in the line of the knuckles to open and close finger armatures over which a cosmetic glove is pulled. A drawback with this device is that the drive train is unable to handle high torques. Moreover, since this device does not drive a thumb, it is of limited use due to its limited pinch force and limited width-of-opening. Another existing externally-powered alternative for persons with partial hand amputations is to use a conventional powered hand and shorten its length. Such shortening enables the use of such devices for short trans-carpal cases. Such device however have limitations in that when shortened, the devices are ill suited for use in transmetacarpal cases.

Various conventional prosthesis mechanisms, some of which have been discussed above, are known and disclosed, for example, in U.S. Pat. No. 5,222,986 to Wright, U.S. Pat. No. 5,888,246 to Gow, U.S. Pat. No. 4,021,866 to Wasko, U.S. Pat. No. 4,291,421 to Massey et al., U.S. Pat. No. 4,258,441 to Bell, U.S. Pat. No. 4,990,162 to Le Blanc et al., U.S. Pat. No. 5,116,386 to Scribner and U.S. Pat. No. 4,865,929 to Eck, the respective disclosures of which are incorporated herein by reference. As discussed above, none of the prosthesis mechanisms disclosed in the above-identified U.S. patents overcome the aforementioned exemplary drawbacks in currently available prosthesis mechanisms.

Accordingly, there remains a need for a hand prosthesis, which may be adequately retained on a user's hand, is cosmetically acceptable and pleasing, does not require a harness to be worn around the shoulders, is suitable for amputations at the meta-carpophlangeal level, and preserves residual wrist motion. There also remains a need for a hand prosthesis which is robust in design, efficient to operate, simple to assemble and disassemble, and which is economically feasible to manufacture.

SUMMARY OF INVENTION

The invention solves the problems and overcomes the drawbacks and deficiencies of the prior art prosthesis devices by providing an externally powered hand prosthesis mechanism for use with persons with amputations at or proximal to the level of the metacarpophalangeal joint, as well as persons with high-level amputations.

Thus exemplary aspects of the present invention are to provide a hand prosthesis, which may be adequately retained on a user's hand, which does not require a harness to be worn around the shoulders, and which preserves residual wrist motion.

The present invention achieves the aforementioned exemplary aspects by providing an externally-powered prosthesis mechanism usable with persons with amputations at or proximal to the level of the metacarpophalangeal joint, as well as persons with high-level amputations. The prosthesis mechanism may include a grasping mechanism including at least one mechanically operable finger member and at least one mechanically operable thumb member kinematically linked to the finger member such that the grasping mechanism is disposed in respective opened and closed configurations when the finger member is respectively moved away from and toward the thumb member. The prosthesis mechanism may further include a drive system extending tangentially with respect to the grasping mechanism. The drive system includes a motor operatively connected to drive at least one planetary gear stage. The planetary gear stage is operatively connected to drive the grasping mechanism to the opened configuration when the motor is driven in a first direction and further drive the grasping mechanism to the closed configuration when the motor is driven in a second opposite direction.

For the prosthesis mechanism described above, the planetary gear stage may include at least one input and at least one output planetary gear stage. The motor may be operatively connected to drive the input planetary gear stage, the input planetary gear stage may be operatively connected to drive the output planetary gear stage, and the output planetary gear stage may be operatively connected to drive the grasping mechanism to the opened configuration when the motor is driven in the first direction and further drive the grasping mechanism to the closed configuration when the motor is driven in the second opposite direction. The input planetary gear stage may be disposed within a drive housing including an axle integrally formed thereon. The finger member may include an integrally formed sleeve rotatably disposed on the axle to thereby enable pivotal movement of the finger member about the axle by means of the input planetary gear stage. A TEFLON bearing may be disposed between the sleeve and the axle. The output planetary gear stage may be disposed tangentially with respect to the sleeve to thereby enable pivotal movement of the finger member by means of the output planetary gear stage being driven by the input planetary gear stage. The prosthesis mechanism may further include a backlock assembly disposed between the input and output planetary gear stages. The backlock assembly may include a casing having a carrier and cam assembly disposed therein, the cam being rotatable in a predetermined direction to wedge at least one roller against an interior wall of the casing to limit rotation of the finger and thumb members. The motor may include a drive shaft, such that the input and output planetary gear stages and the drive shaft include a generally common central axis. The input planetary gear stage may include three planetary gear stages, each of the gear stages including three planet gears operatively driven by the motor to generate a pinch force of at least 5 $lbs_f$ between the finger member and the thumb member, and an opening/closing speed of at least 2 rads/sec for the finger and thumb members. Electrodes may be connected to the motor at one end thereof, the other end of the electrodes being operatively connected to a control system for opening/closing the grasping mechanism using electromyographic sites on a person. The prosthesis mechanism may further include a covering of aesthetically acceptable material having an appearance generally similar to that of a normal hand, and the grasping mechanism may be made of metal.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE PREFERRED EMBODIMENTS

Figure 1:
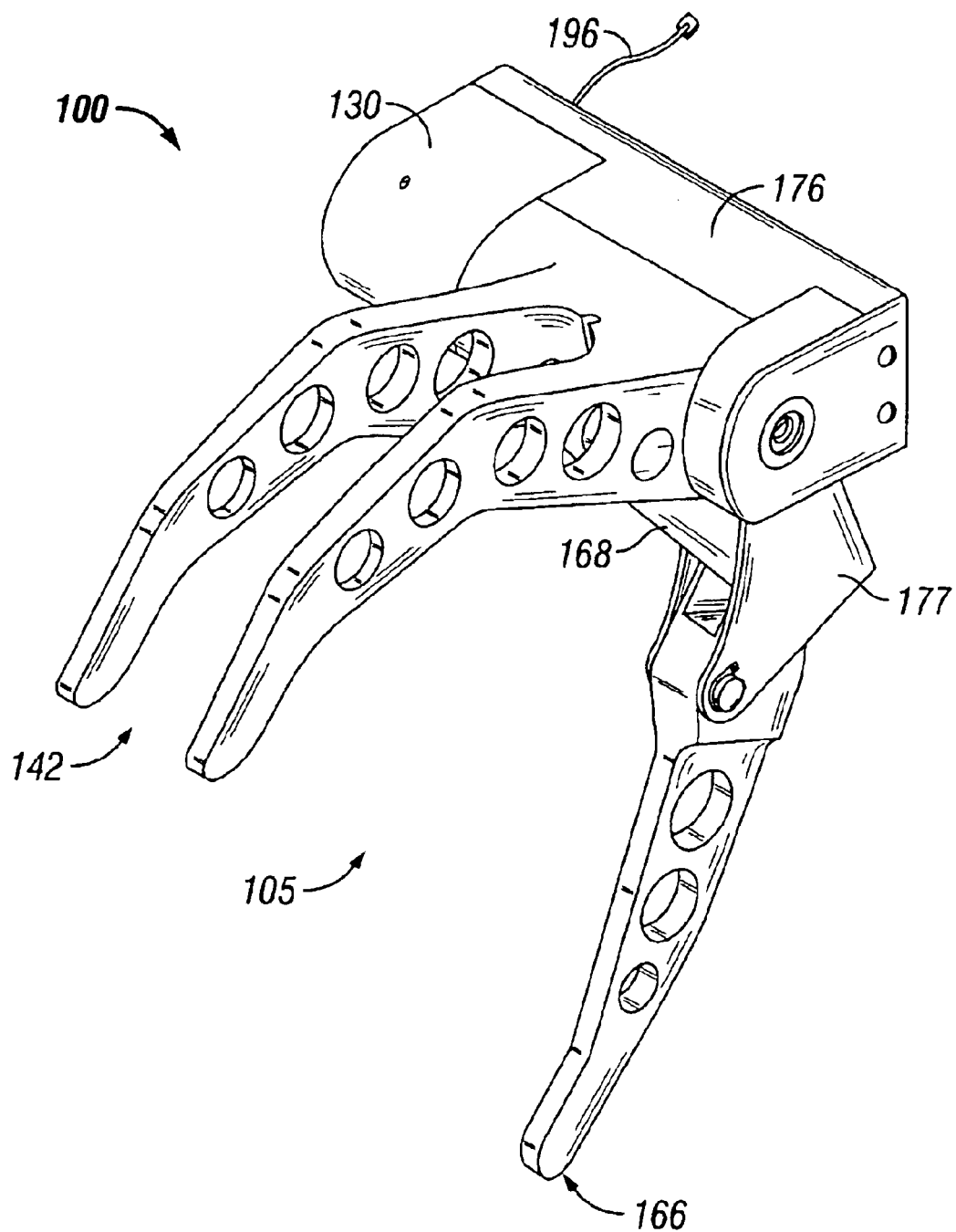
FIG. 1 is an assembled isometric view of the externally-powered hand prosthesis mechanism according to the present invention, illustrating the grasping mechanism in the open configuration.
Figure 2:
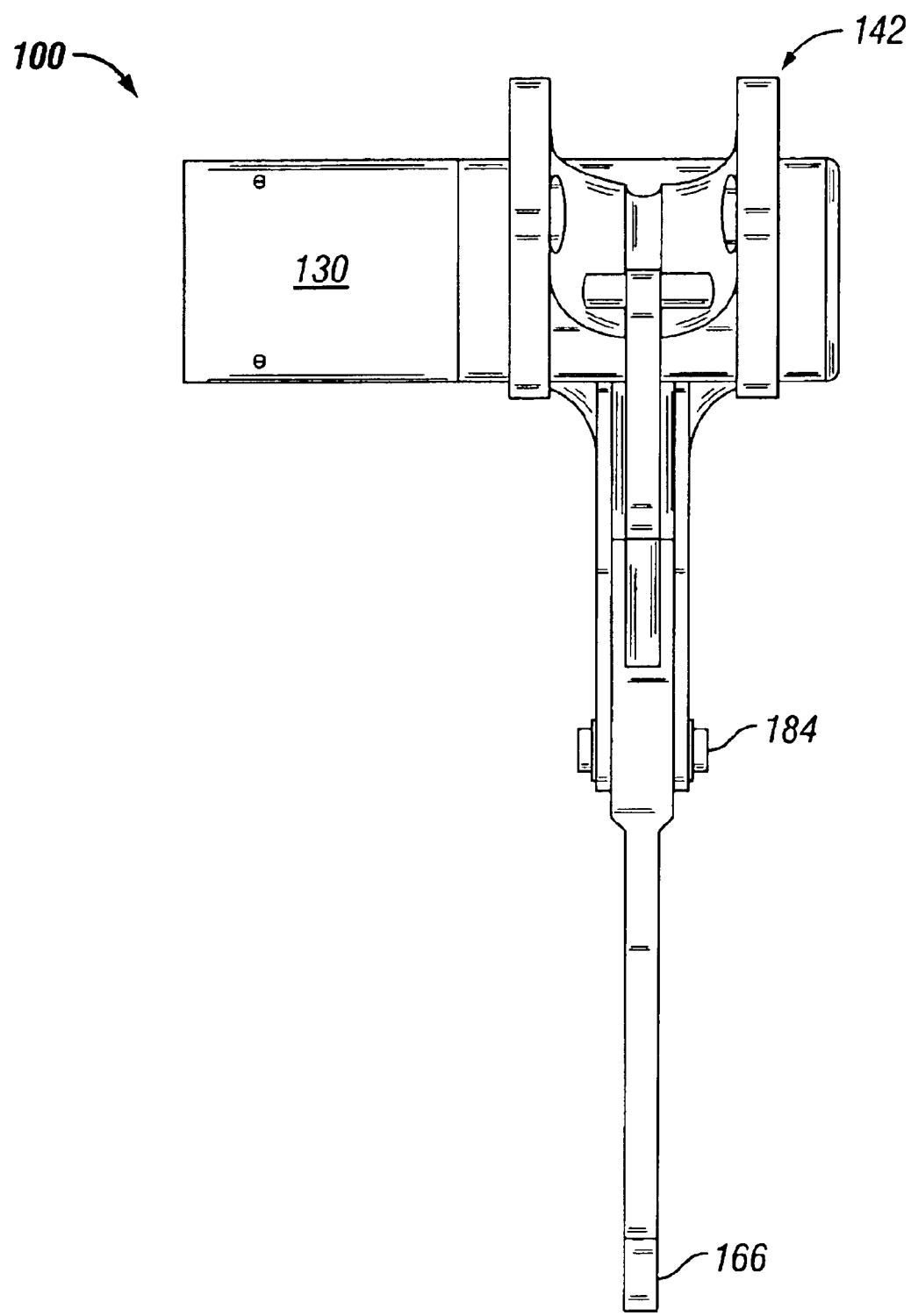
FIG. 2 is a front view of the prosthesis mechanism of FIG. 1.

Referring now to the drawings wherein like reference numerals designate corresponding parts throughout the several views, FIGS. 1–10 illustrate components of the externally-powered hand prosthesis 100 according to the present invention, hereinafter generally referred to as "prosthesis mechanism 100."

As shown in FIGS. 1–10, the present invention provides a highly compact externally powered hand prosthesis mechanism 100 for use by persons with amputations at or proximal to the level of the metacarpophalangeal joint (i.e. persons who have lost one or all digits (thumb and fingers) but still retain a palmar surface of the hand, and persons with high-level (i.e. above-elbow) amputations where weight considerations are of paramount importance. As discussed above, generally a prosthesis is only recommended for cases where all digits (thumb and all four fingers) have been lost at a level equal or proximal to the metacarpophalangeal joint.

The majority of mechanical hands that are currently available for persons with trans-radial (below-elbow) and trans-humeral (above-elbow) amputations are not suitable for persons with wrist disarticulations or partial-hand amputations because the resulting prostheses are too long. A powered-partial hand prosthesis is needed because, although a wide range of devices have been fabricated for partial hand amputees, there are no partial-hand prostheses that provide prehension and are cosmetically feasible for persons with trans-metacarpal amputations.

Figure 6:
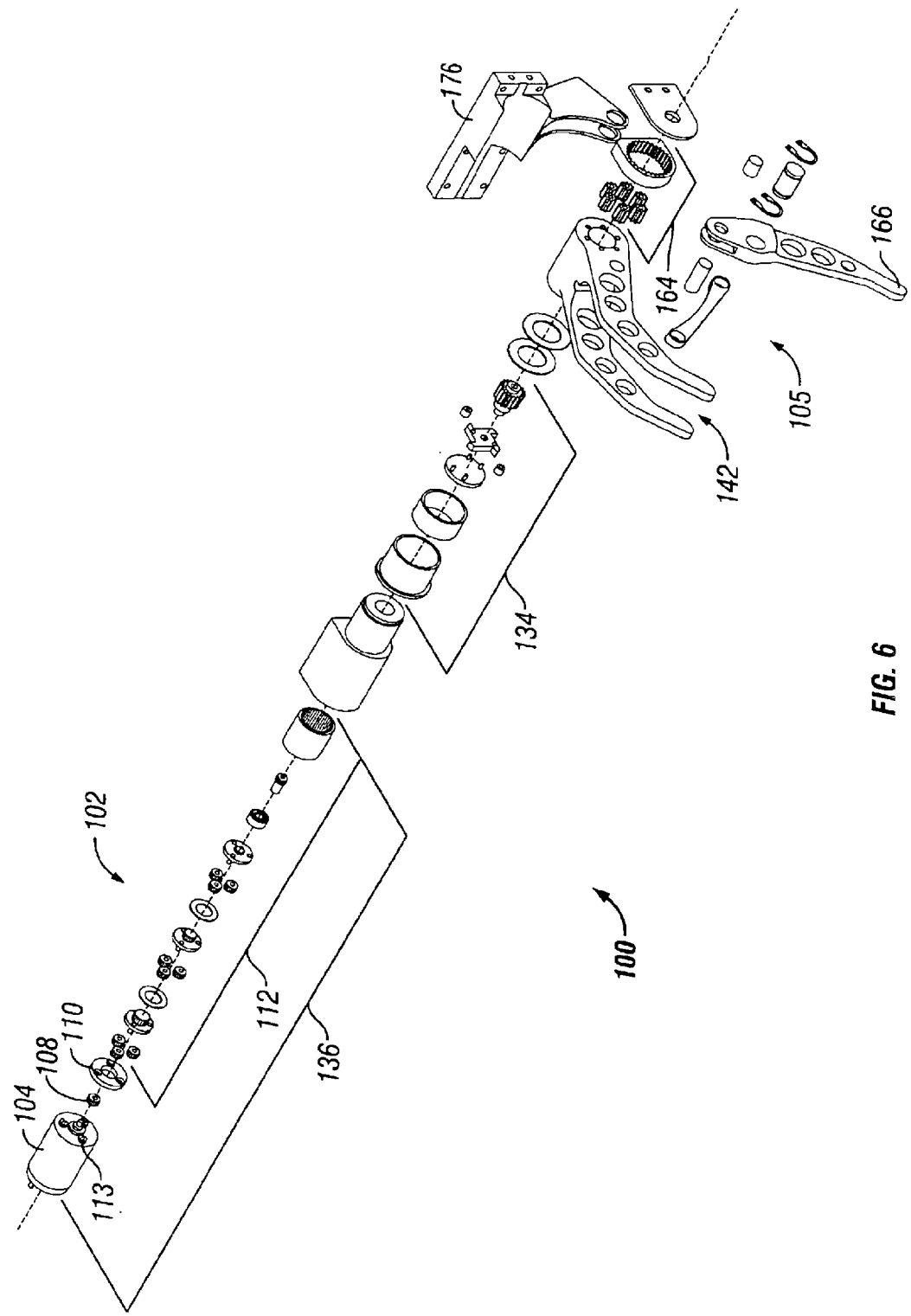
FIG. 6 is an exploded view of the prosthesis mechanism of FIG. 1, illustrating the various components of the mechanism.
Figure 7:
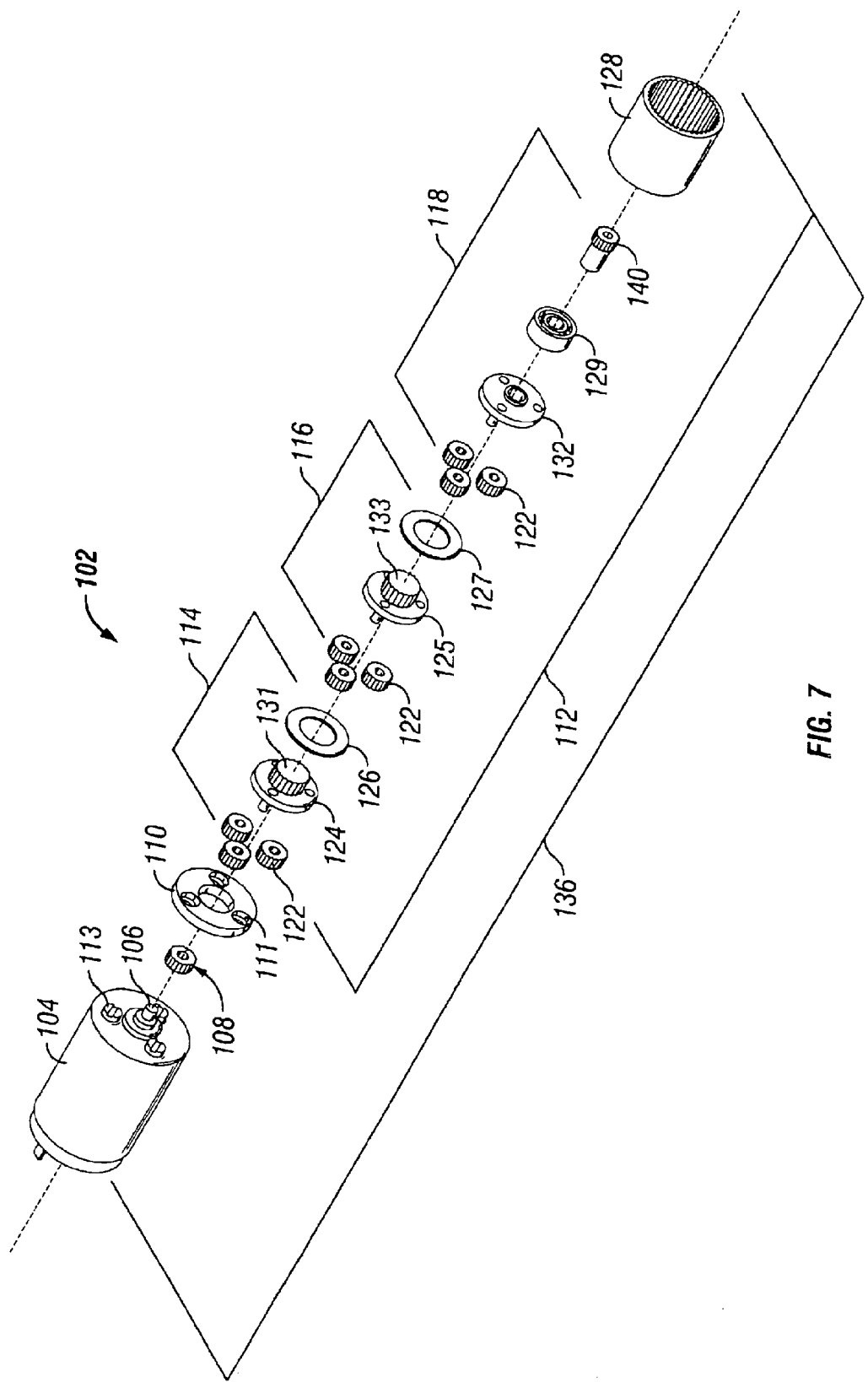
FIG. 7 is an enlarged exploded view of the prosthesis mechanism of FIG. 1, illustrating the motor and geartrain assembly.

As shown in FIGS. 1 and 6, prosthesis mechanism 100, which overcomes the aforementioned exemplary drawbacks and deficiencies of existing prosthesis mechanisms, may generally include drive system 102 for operating fingers 142 and thumb 166 of grasping mechanism 105, with system 102 and mechanism 105 being described in detail below.

Referring to FIGS. 1–7 and 9, drive system 102 may include motor 104, which in the embodiment of FIG. 1 may be a MicroMo MM1724 3 volt motor that is overvoltaged to boost its performance. Since the overall width of prosthesis mechanism 100 is designed to be less than the width of a typical user's hand, as compared to standard component lengths for a MicroMo MM1724 motor, motor 104 may include a reduced length output shaft 106 and likewise a reduced length output pinion 108. A motor gearhead spacer 110 may be mounted to motor 104 by means of screws 113 threaded through guide apertures 111, and may be provided to ensure the proper mating of motor output pinion 108 with the input stage of planetary geartrain 112. The present invention employs a planetary geartrain because of its self-centering capability and because of the equal distribution of torque on the planet gears, thus enabling higher efficiency multistage geartrains. Moreover, the use of a planetary geartrain for the present invention allows for an efficient high gear ratio drive train capable of handling the high torques required to generate acceptable grip forces for grasping mechanism 105.

In the embodiment shown, planetary geartrain 112 may be similar in structure to a MicroMo 16/7 66:1 planetary geartrain. Planetary geartrain 112 may include three input planetary gear stages, which respectively include first, second and third gear stages 114, 116 and 118. Each planetary gear stage may consist of three planet gears 122. In the embodiment of FIGS. 1–9, although three planet gears 122 are shown, the number of gears may be increased or decreased as needed to adjust the grip force of fingers 142 and thumb 166. First planetary gear stage 114 may further include a carrier 124 including an output pinion 131 thereon, and a washer 126. Second planetary gear stage 116 may further include a carrier 125 including an output pinion 133 thereon, and a washer 127. Third planetary gear stage 118 may further include a carrier 132 and a ball bearing 129.

Planetary gear stages 114, 116 and 118 may be operatively disposed within gear housing or annulus 128, which may be disposed within drive housing 130 which also doubles as an axle for prosthesis fingers 142. Carrier 132 of third planetary gear stage 118 may be designed to accommodate a backlock input pinion 140 so that stage 118 mates with the drive stage including backlock assembly 134.

For assembly, planetary gear stages 114, 116 and 118 may be disposed inside annulus 128 and thereafter inserted within drive housing 130. Thereafter, motor gearhead spacer 110 may be disposed in drive housing 130, followed by pinion 108 and motor 104. Thus, as illustrated in FIG. 9, motor 104, pinion 108, spacer 110 and planetary gear stages 114, 116 and 118, all generally referred to as the motor and geartrain assembly 136, may be operatively disposed inside drive housing 130.

Figure 8:
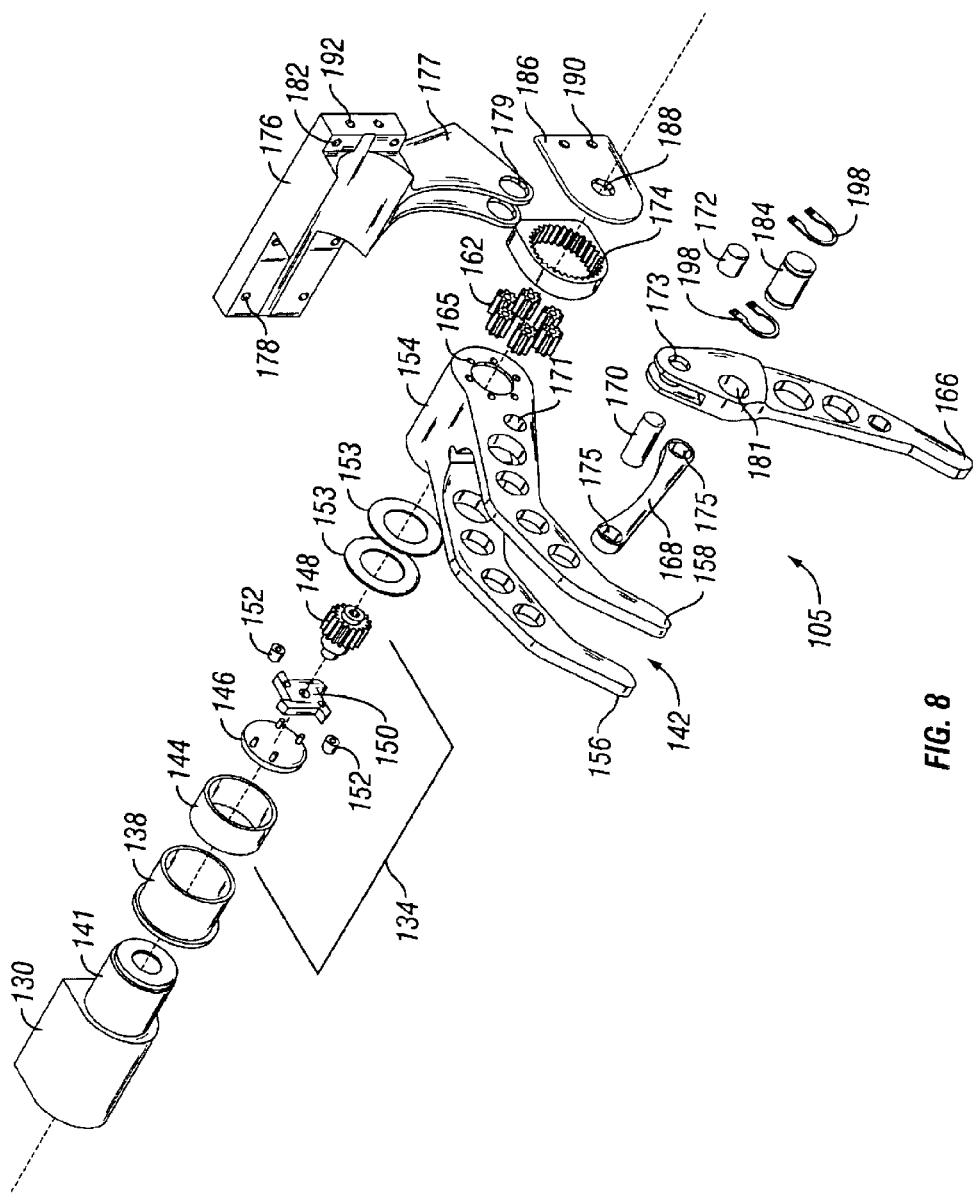
FIG. 8 is an enlarged exploded view of the prosthesis mechanism of FIG. 1, illustrating the drive housing and the grasping mechanism.
Figure 9:
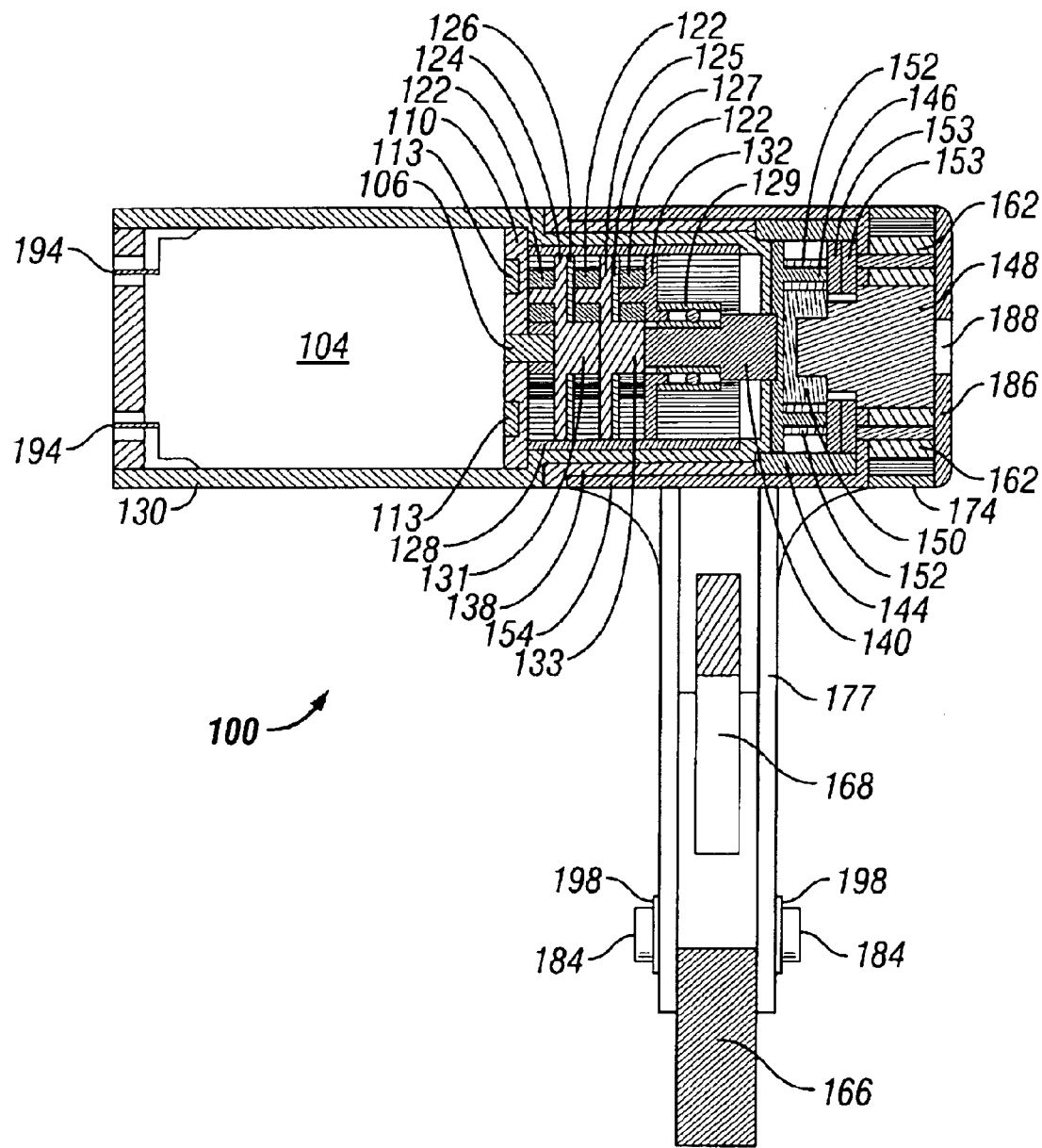
FIG. 9 is a cross-sectional view of the motor and geartrain assembly, taken along section 9—9 in FIG. 4.
Figure 10:
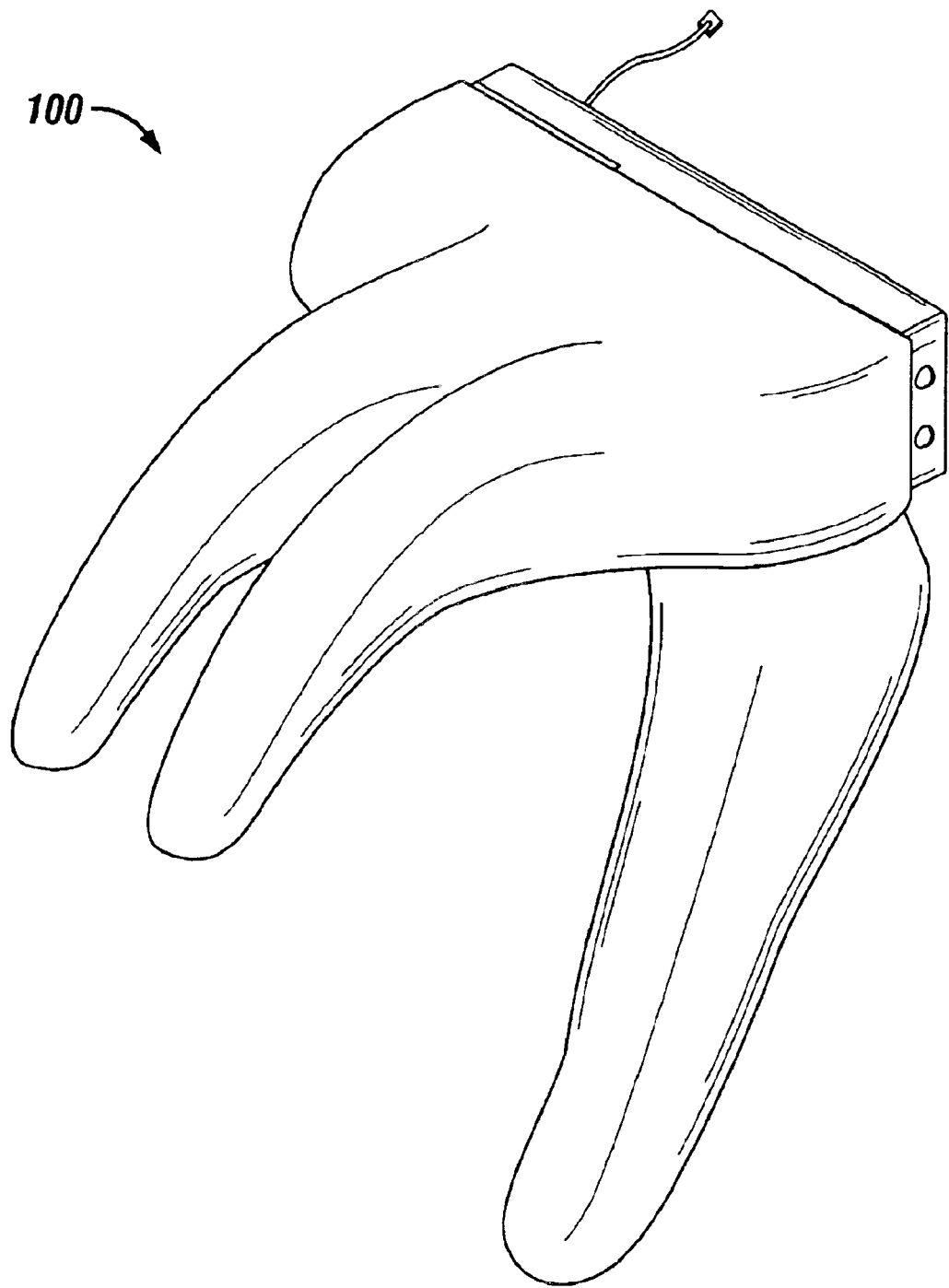
FIG. 10 is a view illustrating a covering on the prosthesis mechanism of FIG. 1.

As shown in FIGS. 8 and 9, a TEFLON impregnated DELRIN finger bearing 138 may be slid over axle portion 141 of drive housing 130 so as to enable free movement of fingers 142 about portion 141.

With motor and geartrain assembly 136 disposed inside drive housing 130, backlock assembly 134 may next be attached to the drive train. Backlock assembly 134, which performs the function of a brake, one-way clutch, or an overrunning clutch, is used to prevent external forces applied at the tips of fingers 142 from opening mechanism 100 when power is discontinued. In this manner, an object may remain grasped even if power to motor 104 is discontinued.

Backlock assembly 134 may include casing 144, carrier 146 disposed within casing 144, and output pinion 148 attached to backlock locking cam 150, to provide output from assembly 134 to output planetary gear stage 164. When rotated in a counter-clockwise direction in the illustration of FIG. 8, cam 150 may be operative to drive/wedge rollers 152 up against the interior wall of casing 144 for preventing further rotation thereof. Backlock assembly 134 may be pinned at four points (not shown) in casing 144, and have a gear ratio of 5.3:1 for the embodiment shown. A pair of thrust washers 153 may be disposed over backlock output pinion 148 to promote free movement of fingers 142 when placed on bearing 138.

Fingers 142 of grasping mechanism 105 may be formed as a single piece of metal and the like, and include integrally formed sleeve 154 that fits over bearing 138 disposed over axle portion 141 of drive housing 130. In the illustrations of FIGS. 1–6, 8 and 9, fingers 142 may include a pair of tines 156, 158 that respectively make up the index and middle fingers, and may include additional tines, as would apparent to those skilled in the art. Sleeve 154 may carry planet gears 162 of final planetary gear stage 164 for mechanism 100. Fingers 142 may be kinematically linked to thumb 166 by means of link 168 having axle 170 disposed within aperture 171 in fingers 142 and axle 172 disposed in apertures 173 in thumb 166, with each of the axles 170 and 172 further disposed within apertures 175 in link 168. In this manner, opening/closing of fingers 142 acts to simultaneously drive thumb 166 to open/close, thus generating a wider opening width for grasping mechanism 105.

Planetary gear stage 164 for driving prosthesis mechanism 100 may use six (6) planet gears 162 mounted on pins at locations 165 in the side of sleeve 154. The use of six (6) planet gears 162 acts to distribute the load that must be handled by each gear, and thus allows mechanism 100 to withstand the high torques necessary to generate a high grip force. Planet gears 162 may exert torque on internal gear 174, which is fixed to frame 176. In the embodiment shown, the gear ratio for planetary gear stage 164 stage may be 2:1. Moreover, in the embodiment of FIGS. 1–6, 8 and 9, although six planet gears 162 are shown, the number of gears may be increased or decreased as needed to adjust the grip force of fingers 142 and thumb 166.

Figure 3:
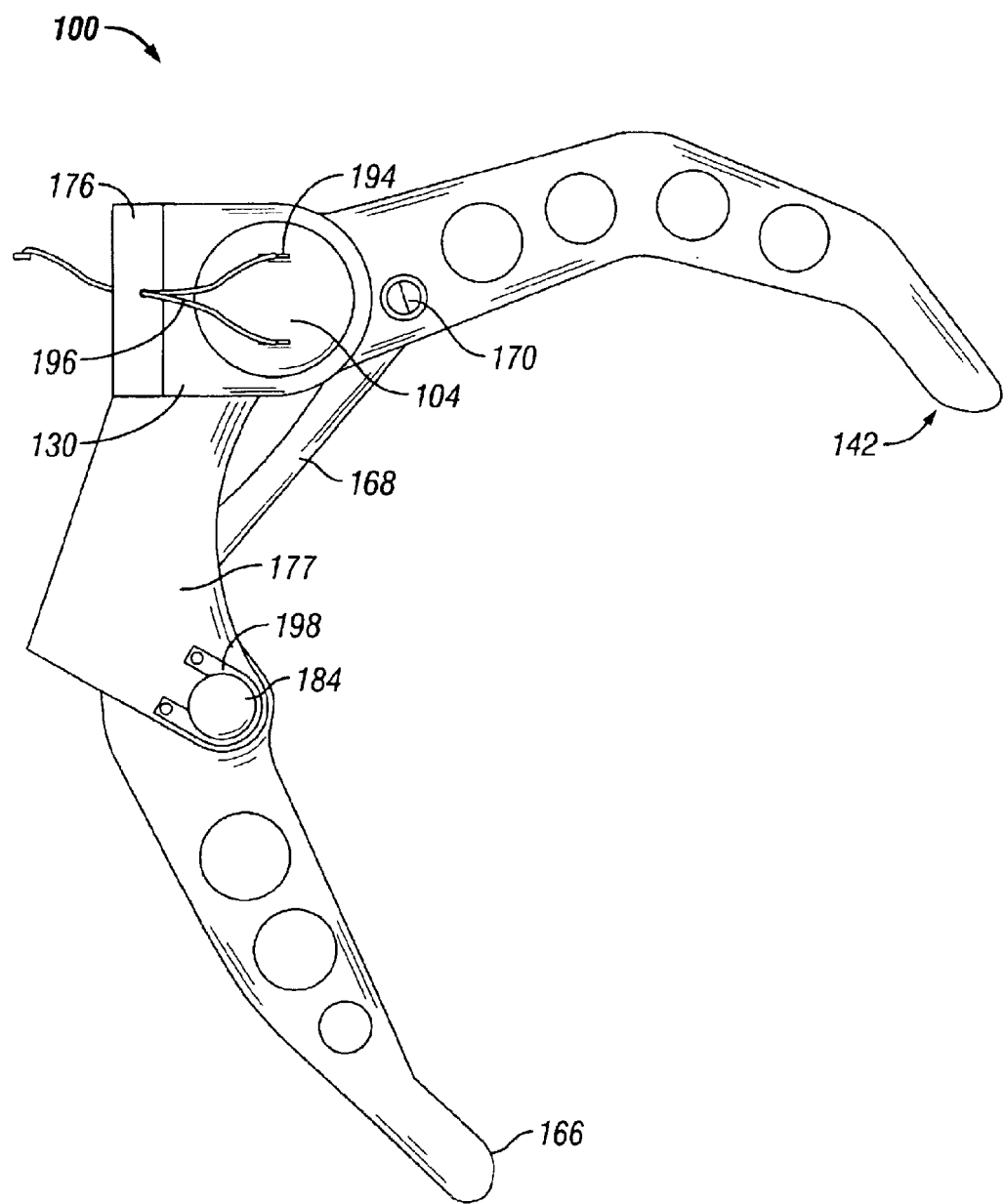
FIG. 3 is a side view of the prosthesis mechanism of FIG. 1.
Figure 4:
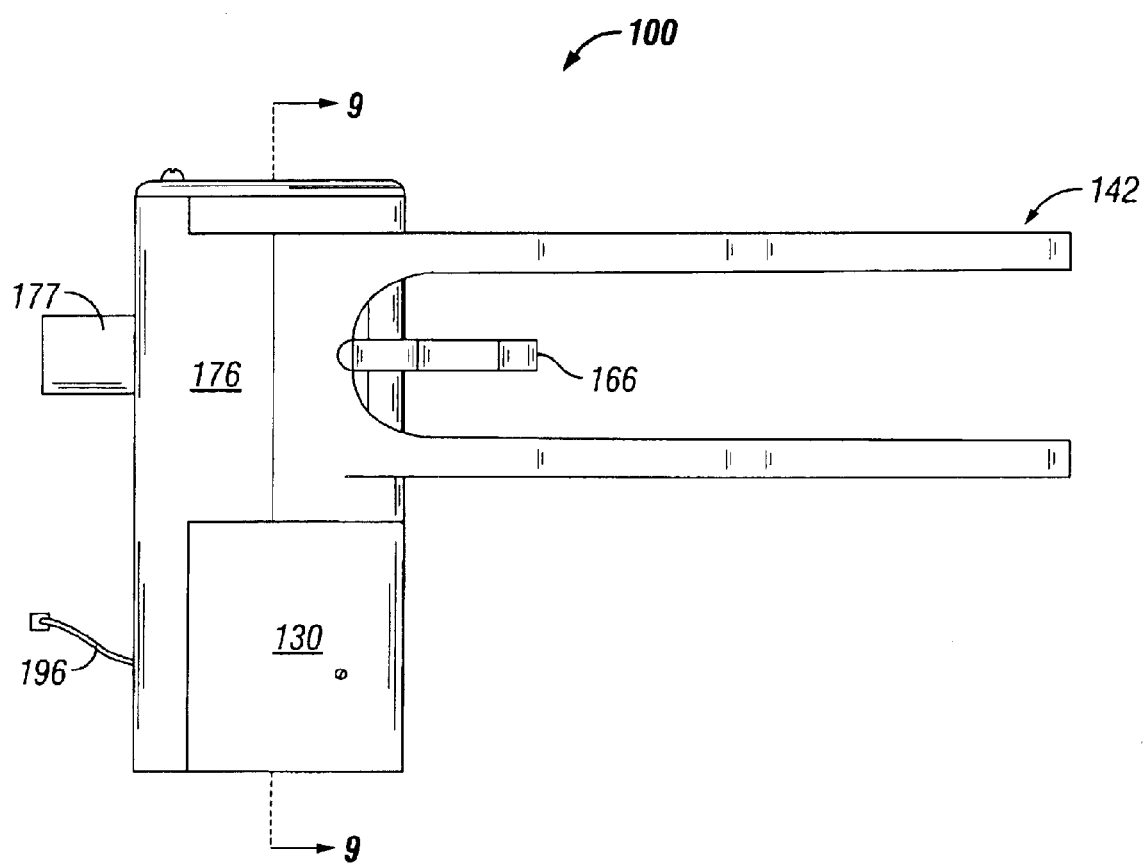
FIG. 4 is a top view of the prosthesis mechanism of FIG. 1.
Figure 5:
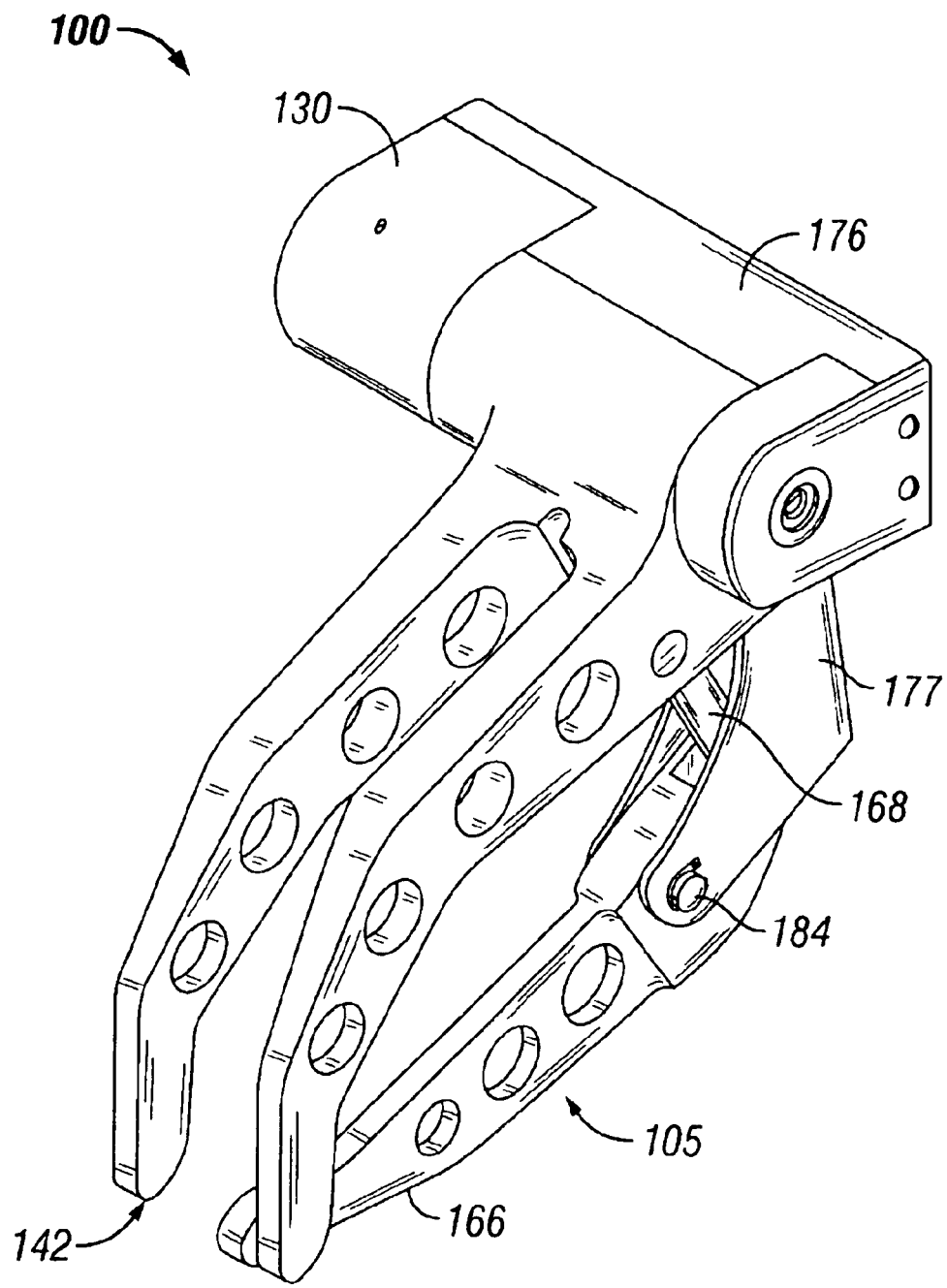
FIG. 5 is an assembled isometric view of the externally-powered hand prosthesis mechanism according to the present invention, illustrating the grasping mechanism in the closed configuration.

Drive housing 130 with sleeve 154 of fingers 142 disposed on bearing 138 may be attached to frame 176 by screws and the like through apertures 178 screwed into threaded apertures (not shown) on the back face of housing 130. Internal gear 174 of the final planetary gear stage 164 may be attached to frame 176 by screws and the like through apertures 182 screwed into threaded apertures (not shown) on the back face of gear 174. Thumb 166 may be attached to extension 177 of frame 176 by an axle 184 disposed into apertures 179 of extension 177 and corresponding aperture 181 of thumb 166. Spring clips 198 may be used to retain axle 184 within aperture 181, as shown in FIG. 3. Lastly, side plate 186 may be attached to the side of frame 176 to close off planetary gear stage 164 by screws and the like through apertures 190 screwed into threaded apertures 192 of frame 176. It should be noted that the shaft of output pinion 148 of the backlock assembly 134 fits in aperture 188 in side plate 186, as illustrated in FIG. 8. In the particular embodiment shown, prosthesis mechanism 100 may have a width of 2¼" and the capability of providing a pinch force for 3" fingers in excess of 10 lbs$_f$ at speeds of approximately 2 rads/sec, with the overall opening width of fingers 142 and thumb 166 being at least 3½".

Those skilled in the art would appreciate in view of this disclosure that due to the compact nature of the resulting drive for mechanism 100, the components that make up the drive train, such as motor and geartrain assembly 136 disposed inside drive housing 130, bearing 138 with backlock assembly 134 attached to drive housing 130 and planetary gear stage 164, have application, when used with frame 176, fingers 142 and thumb 166, as drive trains for other prosthetic components such as wrist rotators, wrist flexion units, or as drive units for multifunctional prosthesis devices.

The operation and control of prosthesis mechanism 100 will now be described in detail.

In normal operation, prosthesis mechanism 100 may be mounted on a prosthetic socket (not shown), in a conventional manner, that has been custom fabricated to fit the residual limb of a person with an amputation of the hand. A cosmetic glove and liner (not shown) may be pulled over mechanism 100 to give it a hand like appearance. As discussed in greater detail below, generally, power supplied to motor 104 at a first polarity causes fingers 142 and thumb 166 of mechanism 100 to open. Power supplied to motor 104 in a reverse polarity causes fingers 142 and thumb 166 of mechanism 100 to close. The opening/closing speed of grasping mechanism 105 and the amount of gripping force may be proportional to the amount of voltage supplied to terminals 194 of motor 104.

In order to connect prosthesis mechanism 100 to a patient's hand, as discussed above, a standard prosthetic interface (not shown) including a self-suspending silicone sleeve-socket may be used to attach mechanism 100 thereon. Fingers 142 and thumb 166 may be incorporated into a silicone sleeve (not shown) made of nylon impregnated with laminating silicone so as to provide resistance to tear and enable various electrodes 196 connected to motor 104 to be pushed through the silicone sleeve and remain in place without tearing the silicone. Electrodes 196 may then be screwed into their electronics, which may be located on the outside of the sleeve. The associated electrode electronics, wires, myocontroller, and synergetic controller may be fitted onto the dorsal surface of mechanism 100 for protection. As discussed above, an outer cosmetic glove may be rolled over this inner silicone sleeve socket. The silicone sleeve socket and cosmetic glove may then be rolled on and off together in a fashion similar that used to donning and doffing transtibial silicone suspension sleeves.

The control system (not shown) for mechanism 100 may include proportional myoelectric control using electromyographic (EMG) sites on a person, as is known in the art. Preferably, mechanism 100 may utilize two EMG sites which use the intrinsic muscles of the hand for control of mechanism 100. For example, the opening of mechanism 100 may be controlled by an electrode over the lateral aspect of the hypo-thenar eminence, and closing could be provided by an electrode over the thenar eminence. Thus, thinking about flexing/adducting the thumb would cause mechanism 100 to close while adducting the little finger would cause mechanism 100 to open. This kind of control might not always be possible, but even if only a single EMG site is available, three-state control may be used.

The power source for motor 104 may be a rechargeable 9V transistor battery so as to enable mechanism 100 to be recharged overnight.

In employing transversely oriented drive system 102 discussed above, the present invention achieves the driving and space requirements for a partial hand mechanism, for which typically a minimal amount of space is available if an aesthetic result is to be achieved, with the drive system having a knuckle depth of only ¾" and with a hand width of only 2¼", for the particular embodiment illustrated.

The use of a single motor 104 for mechanism 100 of the present invention provides simplicity over prosthesis devices that use two or more motors, with regard to the size, weight and the electronics necessary to coordinate the control of multiple motors.

Thus to summarize, prosthesis mechanism 100 of the present invention may be used with persons with amputations at or proximal to the level of the metacarpophalangeal joint (i.e. persons who have lost one or all digits (thumb and fingers) but still retain a palmar surface of the hand, and persons with high-level (i.e. above-elbow) amputations where weight considerations are of paramount importance). Prosthesis mechanism 100 of the present invention is applicable in the prosthetic restoration of prehension in trans-metacarpal partial hand, and wrist disarticulation amputations, as well as trans-radial and trans-humeral amputations.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. An externally-powered prosthesis mechanism usable with persons with amputations at or proximal to the level of the metacarpophalangeal joint, as well as persons with high-level amputations, said prosthesis mechanism comprising:

a grasping mechanism including at least one mechanically operable finger member and at least one mechanically operable thumb member kinematically linked to said finger member such that said grasping mechanism is disposed in respective opened and closed configurations when said finger member is respectively moved away from and toward said thumb member; and a drive system extending tangentially with respect to said grasping mechanism, said drive system including a motor operatively connected to drive at least one planetary gear stage, said planetary gear stage being operatively connected to drive said grasping mechanism to said opened configuration when said motor is driven in a first direction and further drive said grasping mechanism to said closed configuration when said motor is driven in a second opposite direction, wherein said planetary gear stage includes at least one input and at least one output planetary gear stage, said motor is operatively connected to drive said input planetary gear stage, said input planetary gear stage is operatively connected to drive said output planetary gear stage, said output planetary gear stage being operatively connected to drive said grasping mechanism to said opened configuration when said motor is driven in said first direction and further drive said grasping mechanism to said closed configuration when said motor is driven in said second opposite direction, and wherein said motor includes a drive shaft, said input planetary gear stage and said drive shaft include a generally common central axis, such that said externally-powered prosthesis mechanism is usable with persons with amputations at or proximal to the level of the metacarpophalangeal joint, as well as persons with high-level amputations.

2. A prosthesis mechanism according to claim 1, wherein said input planetary gear stage is disposed within a drive housing including an axle integrally formed thereon, said finger member includes an integrally formed sleeve rotatably disposed on said axle to thereby enable pivotal movement of said finger member about said axle by means of said input planetary gear stage.

3. A prosthesis mechanism according to claim 2, further comprising a TEFLON bearing disposed between said sleeve and said axle.

4. A prosthesis mechanism according to claim 2, wherein said output planetary gear stage is disposed tangentially with respect to said sleeve to thereby enable pivotal movement of said finger member by means of said output planetary gear stage being driven by said input planetary gear stage.

5. A prosthesis mechanism according to claim 1, further comprising a backlock assembly disposed between said input and output planetary gear stages, said backlock assembly including a casing having a carrier and cam assembly disposed therein, said cam being rotatable in a predetermined direction to wedge at least one roller against an interior wall of said casing to limit rotation of said finger and thumb members.

6. A prosthesis mechanism according to claim 1, wherein said input planetary gear stage includes three planetary gear stages, each of said gear stages including three planet gears operatively driven by said motor to generate a pinch force of at least 5 lbs$_f$ between said finger member and said thumb member.

7. A prosthesis mechanism according to claim 1, wherein said input planetary gear stage includes three planetary gear stages, each of said gear stages including three planet gears operatively driven by said motor to generate an opening/closing speed of at least 2 rads/sec for said finger and thumb members.

8. A prosthesis mechanism according to claim 1, further comprising electrodes connected to said motor at one end thereof, the other end of said electrodes being operatively connected to a control system for opening/closing said grasping mechanism using electromyographic sites on a person.

9. A prosthesis mechanism according to claim 1, further comprising a covering of aesthetically acceptable material having an appearance generally similar to that of a normal hand.

10. A prosthesis mechanism according to claim 1, wherein paid grasping mechanism is made of metal.

11. An externally-powered prosthesis mechanism usable with persons with amputations at or proximal to the level of the metacarpophalangeal joint, as well as persons with high-level amputations, said prosthesis mechanism comprising:

a grasping mechanism including at least one mechanically operable finger member and at least one mechanically operable thumb member kinematically linked to said finger member such that said grasping mechanism is disposed in respective opened and closed configurations when said finger member is respectively moved away from and toward said thumb member; and a drive system extending tangentially with respect to said grasping mechanism, said drive system including a motor operatively connected to drive at least one planetary gear stage, said planetary gear stage being operatively connected to drive said grasping mechanism to said opened configuration when said motor is driven in a first direction and further drive said grasping mechanism to said closed configuration when said motor is driven in a second opposite direction, wherein said planetary gear stage includes at least one input and at least one output planetary gear stage, said motor is operatively connected to drive said input planetary gear stage, said input planetary gear stage is operatively connected to drive said output planetary gear stage, said output planetary gear stage being operatively connected to drive said grasping mechanism to said opened configuration when said motor is driven in said first direction and further drive said grasping mechanism to said closed configuration when said motor is driven in said second opposite direction, and wherein said input and output planetary gear stages include a generally common central axis.

12. A prosthesis mechanism according to claim 11, wherein said input planetary gear stage is disposed within a drive housing including an axle integrally formed thereon, said finger member includes an integrally formed sleeve rotatably disposed on said axle to thereby enable pivotal movement of said finger member about said axle by means of said input planetary gear stage.

13. A prosthesis mechanism according to claim 12, further comprising a TEFLON bearing disposed between said sleeve and said axle.

14. A prosthesis mechanism according to claim 12, wherein said output planetary gear stage is disposed tangentially with respect to said sleeve to thereby enable pivotal movement of said finger member by means of said output planetary gear stage being driven by said input planetary gear stage.

15. A prosthesis mechanism according to claim 11, further comprising a backlock assembly disposed between said input and output planetary gear stages, said backlock assembly including a casing having a carrier and cam assembly disposed therein, said cam being rotatable in a predetermined direction to wedge at least one roller against an interior wall of said casing to limit rotation of said finger and thumb members.

16. An externally-powered prosthesis mechanism usable with persons with amputations at or proximal to the level of the metacarpophalangeal joint, as well as persons with high-level amputations, said prosthesis mechanism comprising:

a grasping mechanism including at least one mechanically operable finger member and at least one mechanically operable thumb member kinematically linked to said finger member such that said grasping mechanism is disposed in respective opened and closed configurations when said finger member is respectively moved away from and toward said thumb member; and a drive system extending tangentially with respect to said grasping mechanism, said drive system including a motor operatively connected to drive at least one planetary gear stage, said planetary gear stage being operatively connected to drive said grasping mechanism to said opened configuration when said motor is driven in a first direction and further drive said grasping mechanism to said closed configuration when said motor is driven in a second opposite direction, wherein said planetary gear stage includes at least one input and at least one output planetary gear stage, said motor is operatively connected to drive said input planetary gear stage, said input planetary gear stage is operatively connected to drive said output planetary gear stage, said output planetary gear stage being operatively connected to drive said grasping mechanism to said opened configuration when said motor is driven in said first direction and further drive said grasping mechanism to said closed configuration when said motor is driven in said second opposite direction, and wherein said motor includes a drive shaft, said input and output planetary gear stages and said drive shaft include a generally common central axis.

17. A prosthesis mechanism according to claim 16, wherein said input planetary gear stage is disposed within a drive housing including an axle integrally formed thereon, said finger member includes an integrally formed sleeve rotatably disposed on said axle to thereby enable pivotal movement of said finger member about said axle by means of said input planetary gear stage.

18. A prosthesis mechanism according to claim 17, wherein said output planetary gear stage is disposed tangentially with respect to said sleeve to thereby enable pivotal movement of said finger member by means of said output planetary gear stage being driven by said input planetary gear stage.

19. A prosthesis mechanism according to claim 16, further comprising a backlock assembly disposed between said input and output planetary gear stages, said backlock assembly including a casing having a carrier and cam assembly disposed therein, said cam being rotatable in a predetermined direction to wedge at least one roller against an interior wall of said casing to limit rotation of said finger and thumb members.

* * * * *